(12) United States Patent
Farn et al.

(10) Patent No.: US 12,397,068 B2
(45) Date of Patent: Aug. 26, 2025

(54) STRUCTURAL DESIGN OF A CRANIAL NERVE DEGENERATION CONTRAST AGENT PRECURSORS

(71) Applicant: INSTITUTE OF NUCLEAR ENERGY RESEARCH, ATOMIC ENERGY COUNCIL, EXECUTIVE YUAN, Taoyuan (TW)

(72) Inventors: Shiou-Shiow Farn, Taoyuan (TW); Hung-Wen Yu, Taoyuan (TW); Kuan-Yin Chen, Taoyuan (TW); Tsung-Yu Shih, Taoyuan (TW); Yun-Sheng Lin, Taoyuan (TW)

(73) Assignee: INSTITUTE OF NUCLEAR ENERGY RESEARCH, ATOMIC ENERGY COUNCIL, EXECUTIVE YUAN, Taoyuan (TW)

( * ) Notice: Subject to any disclaimer, the term of this patent is extended or adjusted under 35 U.S.C. 154(b) by 585 days.

(21) Appl. No.: 17/943,754

(22) Filed: Sep. 13, 2022

(65) Prior Publication Data
US 2023/0346987 A1    Nov. 2, 2023

(30) Foreign Application Priority Data
Apr. 29, 2022  (TW) .................................. 111116356

(51) Int. Cl.
*A61K 51/04* (2006.01)

(52) U.S. Cl.
CPC ............................... *A61K 51/0446* (2013.01)

(58) Field of Classification Search
CPC ........................... A61K 51/04; A61K 51/0446
See application file for complete search history.

(56) References Cited

U.S. PATENT DOCUMENTS 9,649,392 B2 *   5/2017   Nomoto ............. A61K 49/0004

* cited by examiner

*Primary Examiner* — Michael G. Hartley
*Assistant Examiner* — Jagadishwar R Samala
(74) *Attorney, Agent, or Firm* — Maschoff Brennan

(57) ABSTRACT

Structural design of cranial nerve degeneration contrast agent precursor, the cranial nerve degeneration contrast agent prepared using the cranial nerve degeneration contrast agent precursor can be used for positron radiation tomography to detect alpha-synuclein. Since the cranial nerve degeneration contrast agent has better affinity and specificity for α-synuclein, it is helpful for more efficient early diagnosis of Parkinson's disease.

4 Claims, No Drawings

STRUCTURAL DESIGN OF A CRANIAL NERVE DEGENERATION CONTRAST AGENT PRECURSORS

FIELD OF THE INVENTION

The present invention relates to a contrast agent, and more particularly to a structural design of cranial nerve degeneration contrast agent precursor.

BACKGROUND OF THE INVENTION

Neurodegenerative disease is a disease caused by the chronic atrophy and degeneration of neurons of brain and spinal cord and resulting in loss of function for the neurons. Furthermore, it results in nerve cell death or causes nerve conduction factors reduction or failure absorption of nerve conduction factors. In addition, brain neurons have their functions including movement control, information process, etc., so once the brain neurons are damaged, the irreversible damage in relation to the human cognitive or movement ability will be inevitable.

Parkinson's disease (PD) is the second most common neurodegenerative disease whose one major pathogenic mechanisms is strongly connected to huge amount of misfolded alpha-synuclein (α-syn) accumulation. The patient's brain may accumulate misfolded α-synuclein protein due to gene mutation or the induction of external environmental factors to thus form the pathological structure of Lewy body, resulting in degeneration of dopamine nerve endings in the striatum. In addition, the significant death of dopamine neurons in the substantia nigra pars compacta (SNPc) leads to insufficient dopamine secretion. The above two situations inhibit the conduction pathway from the basal ganglia to the motor cortex nerve, thereby affecting the motor nervous system or causing the combination of non-motor symptoms, resulting in symptoms such as involuntary shaking of the hands, difficulty moving, dysphasia, depression and anxiety.

Many public health organizations have begun to pay high attention and management to Parkinson's disease. In nowadays, the main clinical method for diagnosing a patient with Parkinson's disease is still applying the neuropsychological assessment and the staining method of brain neuropathology of the past century. However, when a patient is diagnosed with Parkinson's disease by the assessment, cerebral neuropathy has usually progressed to a severe stage with obvious symptoms and the treatment of the patient is no longer effective.

According to research, the accumulation of diseased proteins in the brain of Parkinson's disease patients will occur prior to the clinical symptoms. It is equally important to detect the existence and changes of these mutant proteins before the onset of the disease and to provide doctors and patients with the most accurate and accurate information in real time. Therefore, in recent years, radiographic contrast agents have also been used to mark these diseased proteins and positron emission tomography (PET) has been performed in order to achieve early diagnosis, improve the effective treatment of early symptoms and improve the efficiency of clinical trials of therapeutic drugs.

However, among the compounds commonly used in imaging at present, 3-(benzylidine)indolin-2-one shows the ability of binding to pathogenic proteins of Alzheimer's disease such as α-synuclein (α-syn), β-amyloid (Aβ) and Tau proteins. 3-(benzylidine)indolin-2-one has a moderate affinity for α-synuclein and has low specificity for β-amyloid and Tau protein. In addition, many phenothiazine analogs, including the tricyclic SIL23, SIL5, SIL26, fluorescent dyes LDS 798 and LDS 730, show reasonable degree in vitro specificity for α-synuclein as compared to β-amyloid and Tau proteins and show moderate affinity for α-synuclein, but low in vitro stability. The aforementioned phenomenon limits its utility for the existing imaging compounds as a PET contrast agent for Parkinson's disease. Therefore, it is necessary to develop new chemical core structures for Parkinson's disease as lead compounds and for application in PET contrast agents.

In designing probes capable of imaging α-synuclein aggregates, the first step typically involves finding suitable lead compounds to meet a structure-activity relationship. According to the research of Prof. Mach from Massachusetts General Hospital and Washington University School of Medicine in 2015 showed that the compound benzylidene-indolin-2-one (5,3-(benzylidine)indolin-2-one), as shown in general formula 1, was confirmed to be compatible with α-synuclein, β-amyloid and Tau protein, which has moderate affinity for α-synuclein fibrils and low specificity for Aβ and Tau fibrils. In addition, many phenothiazine (phenothiazine) analogs, including tricyclic SIL23, SIL5 and SIL26 as shown in general formula 1, fluorescent dyes LDS 798 and LDS 730, show reasonable degree in vitro specificity for α-synuclein relative to Aβ and Tau proteins, but low in vitro stability and moderate affinity for α-synuclein. The aforementioned phenomenon limits its utility as a positron tomography (PET) imaging agent. Therefore, it is necessary to develop new chemical core structures as lead compounds for application in PET radiotracers.

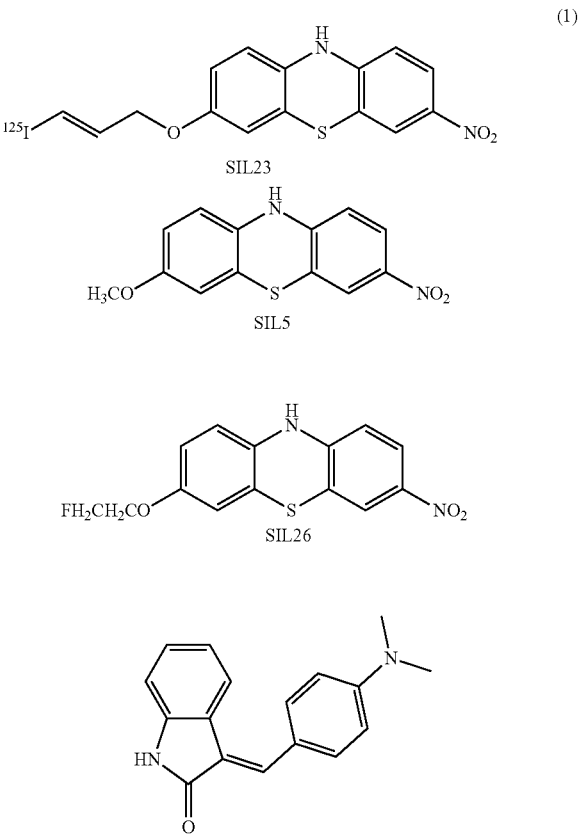

(1)

-continued

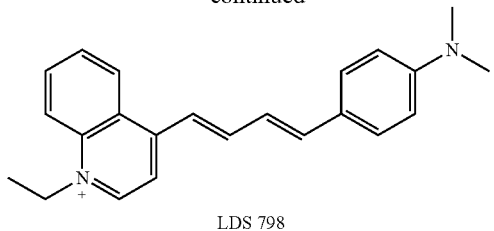

LDS 798

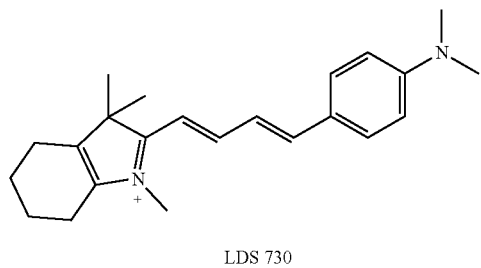

LDS 730

SUMMARY OF THE INVENTION

Accordingly, it is an objective of the present invention to provide a structural design of cranial nerve degeneration contrast agent precursor represented by the following general formula (2):

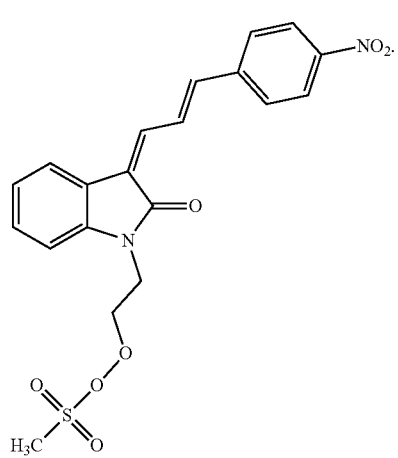

(2)

In an embodiment, the present invention provides a cranial nerve degeneration contrast agent formed by attaching a radioactive isotope fluorine-18 to the cranial nerve degeneration contrast agent precursor described above.

In an embodiment, the present invention provides a cranial nerve degeneration contrast agent as described above, wherein the cranial nerve degeneration contrast agent is a contrast agent for detecting α-synuclein.

In an embodiment, the present invention provides a cranial nerve degeneration contrast agent as described above, wherein cranial nerve degeneration contrast agent is a contrast agent for positron emission tomography.

The inventors of the present invention took the main structure indolin-2-one of compound 5 as shown in general formula 1 as the core structure, and introduced the para-nitro-benzene-allylidene with aldol reaction on the $3^{rd}$ carbon atom. Wherein Engineered allylidene fragments associated with Lewy bodies, which can be labeled with fluorescent dyes LDS 798 and LDS 730 in postmortem specimens from Parkinson's disease. Lewy bodies are dense cores of insoluble α-synuclein deposits in neuronal cells, mainly located in the brainstem and subcortical regions of the central nervous system, therefore, we can import the allylidene fragments in the LDS 798 and LDS 730 structures into indolinones in the hope of increasing the affinity and specificity for α-synuclein.

The inventors further based on the prior art which the branched structure on the nitrogen atom of compound 49 as shown in general formula 3, ethoxy benzyl ether, can reduce the affinity for Aβ and Tau protein, takes the advantage of its structure, and uses $S_N2$ reaction to introduce an ethoxy-alkyl structure to the nitrogen atom to become 2-{3-(Nitrophenyl)allylidene-2-oxoindolin-1-yl}ethoxyethylmethane sulfonate as shown in general formula 4, wherein nitro group is favorable for separation and purification, and methyl sulfonate group is favorable for the substitution reaction of fluorine-18, and it is expected to improve the affinity for α-synuclein and reduce the affinity for Aβ and Tau protein.

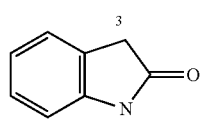

3

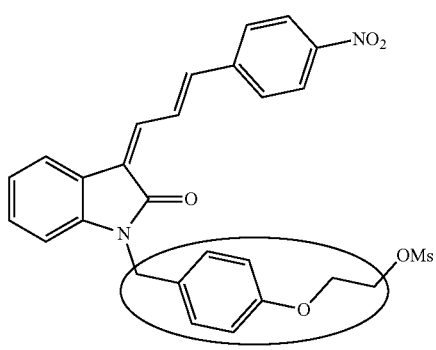

(3)

49

-continued (4)

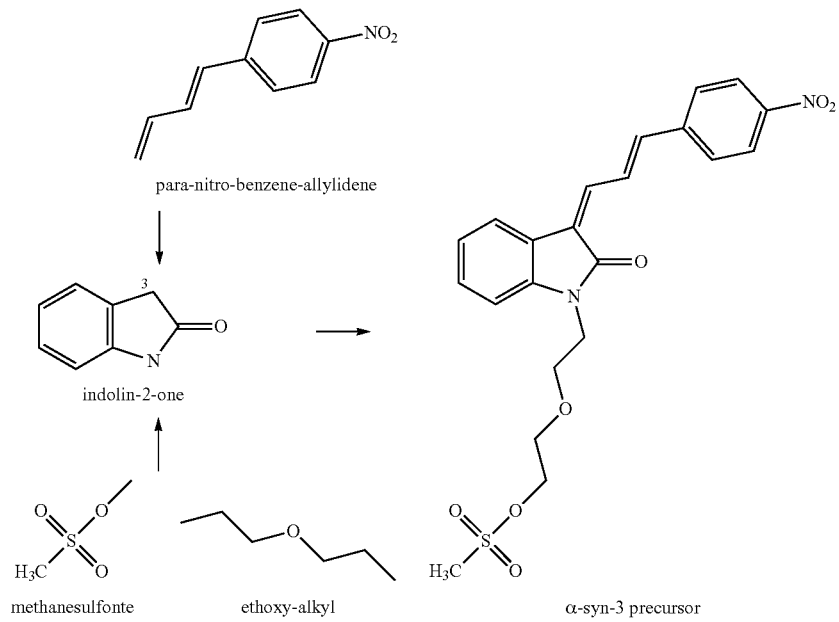

The cranial nerve degeneration contrast agent according to the present invention can be used for positron emission tomography to detect α-synuclein. Since the cranial nerve degeneration contrast agent has better affinity and specificity for α-synuclein, it is helpful for more efficient early diagnosis of Parkinson's disease.

DETAILED DESCRIPTION OF THE PREFERRED EMBODIMENTS

The preferred embodiments of the present invention are described in detail below. The description is for explaining the embodiments of the present invention only, but not for limiting the scope of the claims.

An embodiment of the present invention will be described with reference to the general formula (4), wherein the present embodiment takes indolin-2-one as the core structure.

As shown in the general formula (4), a para-nitro-benzene-allylidene structure is introduced into the carbon atom at the 3$^{rd}$ position of the indolinone using an aldol reaction.

Fluorescent dyes LDS 798 and LDS 730 are known to be associated with the labelling of Lewy bodies, which are insoluble dense structures composed of alpha-synuclein deposits and mainly located in the brainstem and subcortical regions of the central nervous system. Therefore, the inventors introduced an allylidene fragment, which is a common effective structure in LDS 798 and LDS 730, into indolinone to increase the affinity and selectivity for α-synuclein.

Next, as shown in the general formula (4), an ethoxy-ethyl (ethoxy-alkyl) structure and a methanesulfonate (methanesulfonate) structure are introduced into the nitrogen atom position of the indolinone by $S_N2$ reaction to form a 2-{3-(Nitrophenyl)allylidene-2-oxoindolin-1-yl}ethoxyethylmethane sulfonate molecule.

It is known that in a compound, the branched structure ethoxy benzyl ether attached to the nitrogen atom of indolinone can reduce the affinity for β-amyloid and Tau protein. Therefore, by introducing the ethoxy-ethyl structure into the indolinone derivative, the affinity for β-amyloid and Tau protein can be reduced, and the specificity for α-synuclein can be further improved.

The methyl sulfonate structure is beneficial to improve the affinity selectivity for α-synuclein and reduce the affinity for β-amyloid and Tau protein, which is further conducive to the substitution reaction of fluorine-18 and is helpful to use the compound as a positron emission tomography contrast agent.

As described above, the cranial nerve degeneration contrast agent precursor of the present invention can be used for positron emission tomography to detect α-synuclein. Since the cranial nerve degeneration contrast agent has better affinity and selectivity to α-synuclein, it is helpful for more efficient early diagnosis of Parkinson's disease.

In another embodiment, the present invention provides a cranial nerve degeneration contrast agent formed by attaching a radioactive isotope fluorine-18 to the cranial nerve degeneration contrast agent precursor described above.

In another embodiment, the present invention provides a cranial nerve degeneration contrast agent as described above, wherein the cranial nerve degeneration contrast agent is a contrast agent for detecting α-synuclein.

In another embodiment, the present invention provides a cranial nerve degeneration contrast agent as described above, wherein cranial nerve degeneration contrast agent is a contrast agent for positron emission tomography.

The above description should be considered as only the discussion of the preferred embodiments of the present invention. However, a person having ordinary skill in the art may make various modifications without deviating from the present invention. Those modifications still fall within the scope of the present invention.

What is claimed is:
1. A structural design of cranial nerve degeneration contrast agent precursor represented by the following general formula (1):

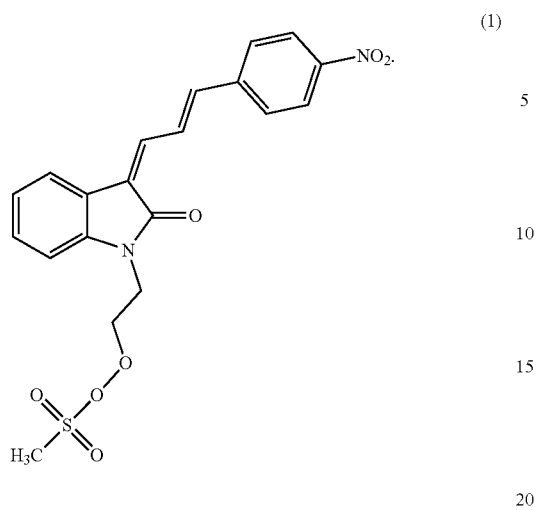

(1)

2. A cranial nerve degeneration contrast agent formed by attaching a radioactive isotope fluorine-18 to the cranial nerve degeneration contrast agent precursor as claimed in claim 1.

3. The cranial nerve degeneration contrast agent as claimed in claim 2, wherein the cranial nerve degeneration contrast agent is a contrast agent for detecting α-synuclein.

4. The cranial nerve degeneration contrast agent as claimed in claim 2, wherein cranial nerve degeneration contrast agent is a contrast agent for positron emission tomography.

\* \* \* \* \*